Sept. 23, 1941. A. KRAMER Plant Pat. 489
CHRYSANTHEMUM PLANT
Filed April 18, 1941
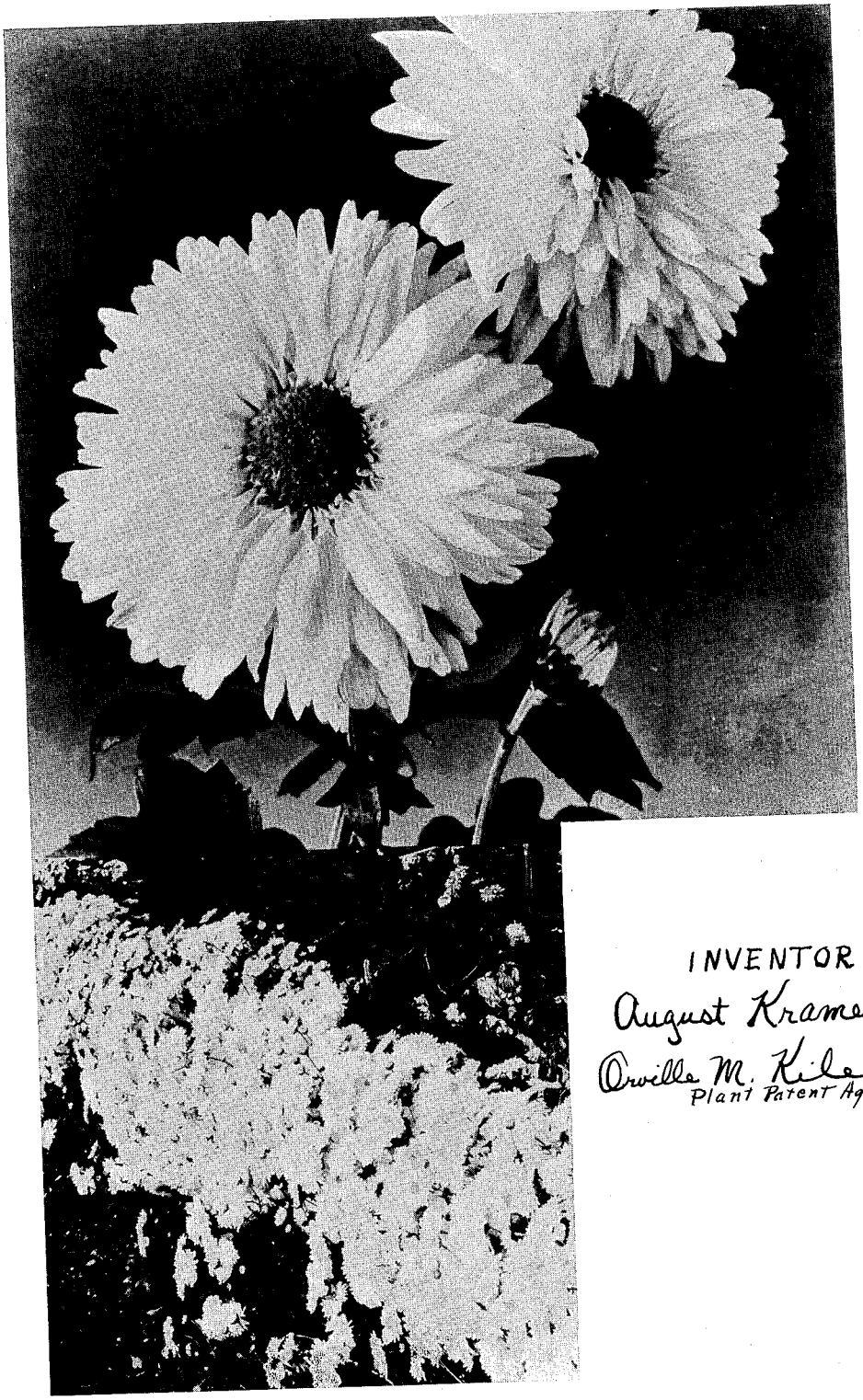
INVENTOR
August Kramer
Orville M. Kile
Plant Patent Agt.

Patented Sept. 23, 1941

Plant Pat. 489

UNITED STATES PATENT OFFICE

489

CHRYSANTHEMUM PLANT

August Kramer, Ontario, Calif., assignor to Kramer Bros. Nurseries, Ontario, Calif.

Application April 18, 1941, Serial No. 389,204

1 Claim. (Cl. 47—60)

This new discovery relates to a new variety of chrysanthemum plant of the multiflowered type. The plant is an upright and vigorous grower and is almost completely covered with blossoms during the blossoming season.

My new variety is a seedling of unknown parentage which was discovered as a single volunteer seedling in a garden containing rows of Garza Supreme and White Supreme.

It has been asexually reproduced through several generations and its distinguishing features have proved to be permanently fixed.

My new variety is unlike other similar varieties in several respects but its chief distinguishing characteristics are its late blooming and the shape of its flower. I know of no other white chrysanthemum of this general type which under similar conditions blooms as late as my new variety. Neither do I know of any other white chrysanthemum with flowers of the same type, being "single" with several whorls of petals (ray flowers) surrounding a not too prominent center, rather than the usual anemone type with exaggerated center.

The original illustrations accompanying this application show a portion of a row of the plants in full bloom, also two slightly enlarged single flowers showing detail.

Following is a detailed description of the plant and flower of this new variety.

*The plant*

Growth:

Sturdy, upright bush, attaining a height of 2½ to 3½ feet. Each plant has 10 to 12 flower sprays when cut back according to commercial practice. Sprays are well branched and bunch gracefully.

Stems:

Rigid; strong; branching; approximately Kronberg's Green (Plate XXXI, Ridgway); somewhat brittle, but soft enough to take water well.

Foliage:

Abundant, particularly at base of plant.

*Color.*—Approximately Yew Green (Plate XXXI, Ridgway), with lighter veining. Under surface is between Cress Green and Dark Cress Green (Plate XXXI, Ridgway) but with a slight gray bloom. Darker than the foliage of most plants of this type of chrysanthemum.

*Shape.*—Palmately lobed, lower lobes usually rather deep but not extending to midrib. Edges somewhat dentate. Pattern of notches is different from that of other varieties.

*Size.*—Medium. Typical leaves measure 2 to 2½ inches wide and 3 to 3½ inches long, including petiole.

Blooming habit:

Flowers bloom evenly. Practically all the blooms on a single plant mature at one time, making the bush almost a solid mass of bloom with very few of the leaves showing except at the base of the plant.

Blooming period:

Blooming dates vary according to weather and light conditions and to the treatment of the plants. In California in our gardens the usual blooming season falls in January, but during the past year our earliest planting began blooming in December. The accompanying illustration shows part of a row of this new variety which was planted in our field on July 15, 1940, cut back September 5th, and photographed on December 20th. Other years have produced a similar show of blossoms on January 10th from plants cut back in September.

*The flower*

Buds:

*Shape.*—Flat-topped and bulging.

*Size.*—Medium.

*Opening.*—Bud opens slowly. Some petals develop more rapidly than others thus making the opening blossom uneven and starlike.

Blossom:

*Forms.*—The flower is not the anemone type as are other white varieties nearest like it, but is the "single" type. It is composed of a relatively small cushion center surrounded by four to eight whorls of petals (or ray flowers). The center is composed of a large number of small tubular florets slightly more than ¼ inch in length and set high upon a pithy base.

*Size.*—Flowers grown outside without disbudding are 2½ to 3 inches in diameter, with a center ¾ to 1 inch in diameter.

*Color.*—Petals (ray flowers) are white with a slightly creamy tinge. Center is approximately Light Cadmium (Plate IV, Ridgway) when the blossom is fully mature. Before maturity the center has a green tinge.

*Petalage.*—There are approximately 125 petals (or ray flowers) arranged in four to eight whorls surrounding the composite center.

*Petals or ray flowers.*—Soft; white; approximately an inch in length; tubular at base, spreading to trough shape in center and slightly reflexed at tip in fully opened blossom.

*Fragrance.*—Characteristic chrysanthemum fragrance.

*Longevity.*—Lasts exceptionally well as a cut flower.

*Comparisons*

The two known varieties which are most like my new variety are the Garza Supreme and the White Supreme. However these varieties differ from my new variety in several respects, particularly as to form of blossom. Principal differences are given below:

1. My new variety is the "single" pompon type having several whorls of petals surrounding a center composed of rather small tubular florets, while the Garza and White Supreme are of the anemone type.
2. My new variety normally blooms somewhat later than Garza when grown under the same conditions, and considerably later than the White Supreme.
3. The foliage of my new variety is much darker than that of either Garza or White Supreme and has an entirely different pattern of notches.
4. The flowers of my new variety all mature at approximately the same time on a single plant, but this is not usual with the Garza or any other variety blooming so late.
5. My new variety is much more vigorous in growth than either of these other varieties.
6. My new variety is much more prolific in its production of blooms than either of the other varieties.

Having thus disclosed my new discovery, I claim:

The new and distinct variety of white multiflowered chrysanthemum plant herein shown and described, characterized particularly by its upright, vigorous growth; the dark color and distinctive pattern of notches of its foliage; its relatively late blooming season; the simultaneous opening of most of the blossoms on a plant; and its prolific production of single blossoms of distinctive form as indicated.

AUGUST KRAMER.